United States Patent [19]

Triller et al.

[11] Patent Number: 5,396,302
[45] Date of Patent: Mar. 7, 1995

[54] APPARATUS FOR PRODUCING THE IMAGE OF AN OBJECT

[75] Inventors: Adolf Triller, Lochham; Ulrich Klingbeil; Andreas Plesch, both of München, all of Germany

[73] Assignee: G. Rodenstock Instrumente GmbH, Ottobrunn-Riemerling, Germany

[21] Appl. No.: 152,095

[22] Filed: Nov. 15, 1993

Related U.S. Application Data

[63] Continuation of Ser. No. 947,993, Sep. 21, 1992, abandoned, which is a continuation of Ser. No. 821,911, Jan. 15, 1992, abandoned, which is a continuation of Ser. No. 459,693, Jan. 29, 1990, abandoned.

[30] Foreign Application Priority Data

Jun. 29, 1988 [DE] Germany ............... 3821975
Jun. 29, 1988 [DE] Germany ............... 3821977

[51] Int. Cl.⁶ .................................... A61B 3/14
[52] U.S. Cl. ......................... 351/206; 351/205
[58] Field of Search .......... 351/205, 206, 207, 208, 351/221; 354/62; 350/6.5, 6.6, 6.7, 6.8; 250/236; 359/196-206

[56] References Cited

U.S. PATENT DOCUMENTS 4,370,034 1/1983 Nohda ..................... 351/206

FOREIGN PATENT DOCUMENTS 8803396 5/1988 WIPO .

Primary Examiner—William L. Sikes
Assistant Examiner—Hung Xuan Dang
Attorney, Agent, or Firm—Antonelli, Terry, Stout & Kraus

[57] ABSTRACT

An apparatus for producing an image of an object and, in particular, for examining the eye, having an illumination light source, the light of which can be focussed onto the section of the object to be examined, a scanning device, which generates a scanning movement of the source of the illumination light over the section to be examined and which is provided with beam-deflecting and image-forming optical elements, a detector device, which receives the light reflected from the section to be examined, and an evaluation and sychronization unit, which produces an image of the selected structures of the object from the time-sequential output signal from the detector device at least two image forming optical elements, which can be interchanged in order to alter the horizontal deflection angle, or image magnification in the horizontal direction, are provided in the beam path between the beam-deflecting elements.

11 Claims, 2 Drawing Sheets

APPARATUS FOR PRODUCING THE IMAGE OF AN OBJECT

This application is a continuation of application Ser. No. 947,993, filed on Sep. 21, 1992, now abandoned which is a continuation of application Ser. No. 821,911, filed Jan. 15, 1992, now abandoned which was a continuation of application Ser. No. 459,693, filed Jan. 29, 1990, now abandoned.

TECHNICAL FIELD OF THE INVENTION

The present invention relates to an apparatus for producing an image of an object and, in particular, for examining the eye.

STATE OF THE ART

The difficulty in examining the posterior portion of the eye is that the illumination and the examination have to be conducted through the pupil and the optically often not clear anterior media of the eye, in which reflexes occur and which cause aberrations.

For some time, therefore, it has been recommended to employ scanning devices that do not illuminate large areas of the posterior portion of the eye, but scan the posterior portion of the eye with as small as possible an illumination beam and note the reflected light in correlation to the scanning sequence instead of using conventional fundus cameras. Reference with regard to this is made, by way of illustration, to "The Foundations of Ophthalmology", Vol. 7, pp. 307/308, 1962, U.S. Pat. No. 4 213 678, Japanese patent publications 61-5730 and 50-138822, and EP-A-0145 563.

The devices known from the afore-cited publications permit surveying the fundus oculi. However, it would be advantageous—as was understood in accordance with the present invention—especially due to the excellent quality of the image delivered by the scanning devices if, particularly in examining the posterior portion of the eye, the section of the image could be varied and if details of it could be magnified.

DESCRIPTION OF THE INVENTION

The object of the present invention is to provide an apparatus for producing an image of an object and, in particular, for examining the eye, which permits varying the size of the portion to be examined and, in particular, magnifying specific areas.

In accordance with the present invention, an arrangement with two lenses or mirrors is proposed, which are arranged in the path of the beam between the elements deflecting the beam, thus by way of illustration between a polygonal mirror and an oscillating, respectively a galvanometer, mirror, and which can be interchanged as "a unit" in order to alter the horizontal deflection angle or image magnification in the horizonal direction.

It is especially advantageous if the two optical elements form an afocal system.

The distance of the optical elements from each other and from the horizontal and vertical deflecting elements may preferably be selected in such a manner that the scale of the image assumes the reciprocal value of the original scale of enlargment when the optical elements are interchanged (horizontal with vertical deflecting elements) as in that case the length of the optical path does not alter, which would require shifting the "reflecting site" during the interchanging. Naturally, other scales may also be selected and the optical elements on the varier may be designed in such a manner that the altered length of the optical path is taken into account during variation.

As the magnifying varier is arranged at a site in the path of the beam, at which the scanning illumination beam fans out only in one direction, namely horizontally, the size of the optical elements can be small. This is especially advantageous in the construction of mirror systems simultaneously the required tilting angle of the mirrors and thus the aberrations are substantially smaller than is the case with a magnifying varier arranged at another site in the overall optical system, namely between the scanning device and the eye.

Employing the mirrors hereto has the advantage over the use of lenses that the system is practically free of reflexes and is achromatic.

The small remaining aberrations of the magnifying varier can be further reduced by employing Mangin mirrors instead of surface-silvered mirrors.

The invented measures described in the foregoing section result in a variation of the scale of the image in a horizontal direction; naturally, similar measures can also "optically vary" the scale of the image in a vertical direction.

It is particularly advantageous, however, if the variation of the vertical magnification in adaption to the altered horizontal magnification due to the exchange of elements ensues by the vertical deflecting device, thus by way of illustration a galvanometer mirror, being triggered accordingly. In a simple manner this may occur electronically.

The invented apparatus permits varying the size of the portion being examined and, in particular, of magnifying specific areas makes sharp focussing appear desirable especially when examining the posterior portion of the eye, by way of illustration in order to compensate for refraction.

One proposed manner of realizing such sharp focussing is already known from EP-A-O 145 563. In this device, the illumination as well as the examination ray of light are guided via the scanning device. The separation into illumination and examination beams of light occurs immediately behind (looking in direction of the reflected light), respectively before (looking in direction of the illuminating light) the scanning device. Means for compensating for refraction, which move synchronously in order to compensate for refraction, are provided in that part of the light path, in which the examination and the illumination beams are separated.

This prior art device for examining the eye has, however, a number of disadvantages.

Firstly, it is necessary to provide means which move the optical components for compensating refraction provided in the respective beam paths synchronously. Secondly, adjustment is very complex as relatively many elements have to be provided for compensating refraction. Moreover, it is practically impossible to alter the length of the optical path with this known device.

A further embodiment of an invented apparatus permitting refraction compensation with good optical properties and technically comparatively simple. This solution in accordance with the present invention can, of course, also be utilized in a similar type apparatus, i.e. in an apparatus without a change in magnification.

An element of the present invention is that it was understood that it is not only possible, but also especially advantageous to arrange the elements for sharp focussing, respectively for compensating refraction, in that part of the light path, which the illumination and the examination beams pass jointly. It is, however, as was also understood in accordance with the present invention, not useful to arrange the means for compensating refraction in the light path of the scanning device or in the light path between the scanning device and the eye, as in that case comparatively large optical elements would be required due to the fanning out of the beam.

For this reason, in accordance with the present invention the means for compensating refraction is arranged between the scanning device and the optical element by means of which the illumination light path and the examination light paths are separated. This element can, by way of illustration, be a divider mirror.

In order to provide the space required for the means for compensating refraction, an intermediate image of the plane of the pupil is formed by means of a "relay system". This intermediate image is produced by an arrangement of at least two lenses and/or mirrors; furthermore, non-image-forming mirrors, which deflect the light path and are jointly shifted in order to vary the path, may be provided in order to compensate for the light path.

Thus, a variation in the divergence of the illumination and examination beams, which compensates for varying refraction, by way of illustration of the eyes to be examined, can be brought about by interchanging, respectively "removing" an image-forming optical element, such as a lens, of a lens system and/or by shifting an image-forming optical element. In addition, these elements enable sharp focussing on different planes within the eye.

Moreover, compared to Webb's proposal, the invented apparatus has the advantage that the plane of the pupil can be placed directly on the scanning element of the scanning device, thus, by way of illustration a polygonal or oscillating mirror, in such a manner that a symmetrical beam path is yielded.

In any event, the invented apparatus has the advantage that refraction compensation is accomplished in a distinctly simpler manner with regard to construction and adjustment than with the state of the art.

BRIEF DESCRIPTION OF THE DRAWING

The present invention is made more apparent in the following section using a preferred embodiment with reference to the accompanying drawing, in which.

DESCRIPTION OF PREFERRED EMBODIMENTS

Figure 1:
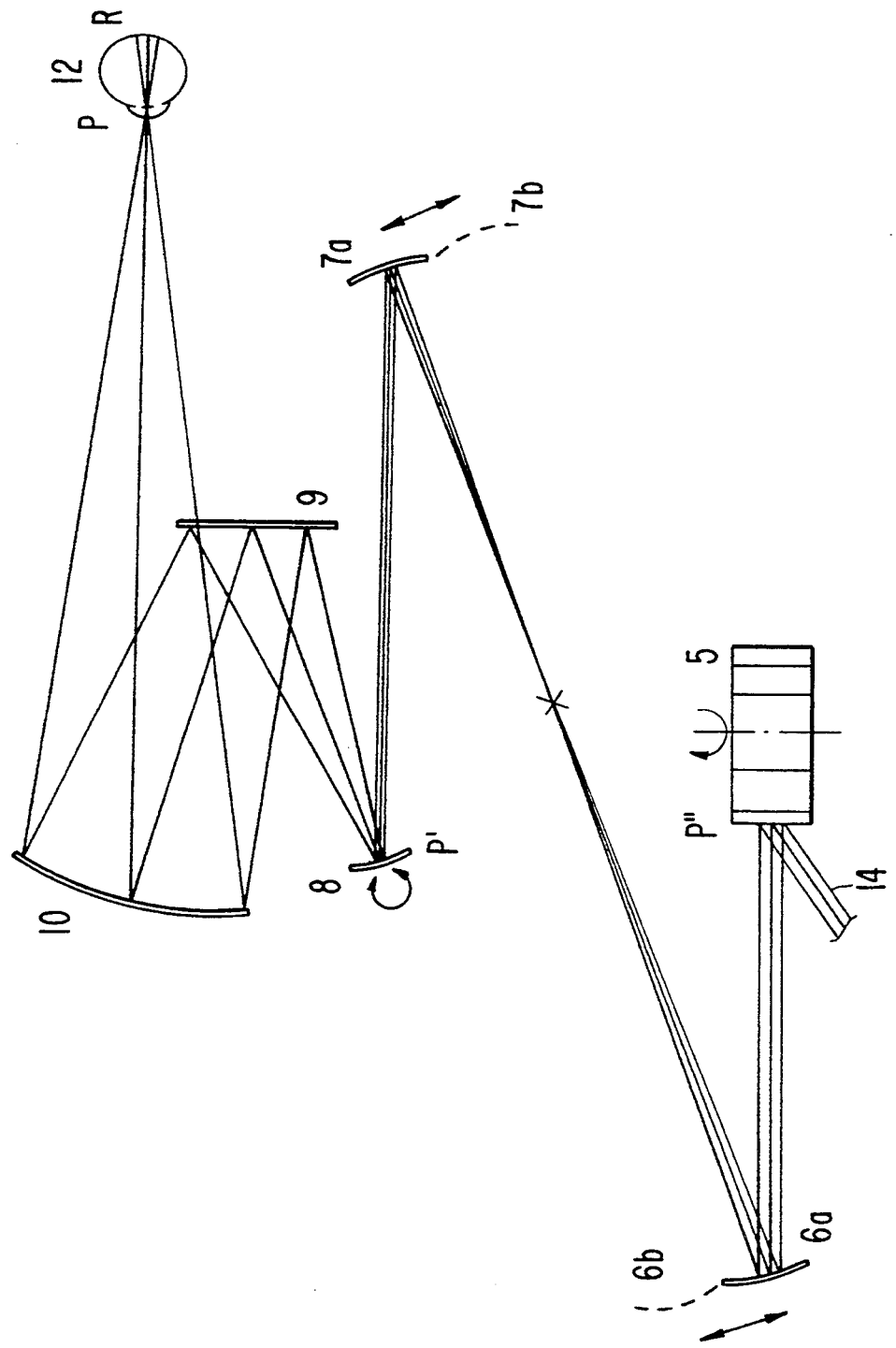
FIG. 1 depicts the invented magnifying variation.
Figure 2:
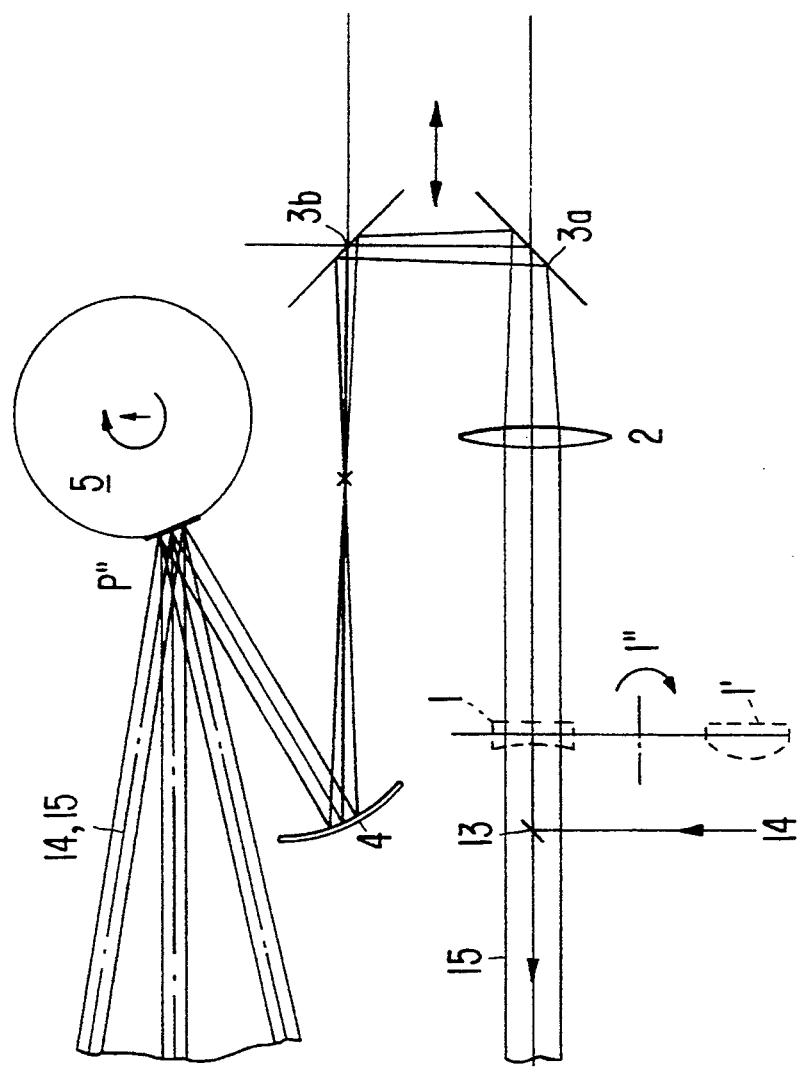
FIG. 2 and the invented sharp focussing.

The invented apparatus is provided with an illumination light source not depicted in FIGS. 1 and 2, by way of illustration a laser, as well as a not depicted detector device, the output signal of which is assessed by an evaluation and synchronisation unit and, by way of illustration, is displayed on a monitor. In the depicted preferred embodiment both the illumination beam 14 and the beam 15 coming from the fundus oculi "run" via the deflection device.

FIG. 1 shows that light beam 14 from the laser is deflected in a horizontal direction (perpendicular to the drawing plane) by the horizontal scanner, which, in the illustrated preferred embodiment, is a rotating polygonal mirror 5. The beam fanning out in the horizontal plane runs through mirror system 6 and 7 and hits a vertical scanner, which, in the illustrated preferred embodiment, is an oscillating, respectively a galvanometer, mirror 8 in the depicted drawing. Behind mirror 8, the bundle of rays has a "rectangular" cross-section. Following deflection at a plane mirror 9, its image is projected by a concave mirror 10 onto the eye to be examined 12. The reflected ray of light 15 runs through the mentioned elements in reverse order and is indicated behind the horizontal deflecting element 5 by a not depicted detector after prior separation of the illumination and the examination light path.

In the illustrated preferred embodiment, in order to alter magnification, elements 6a and 7a can be interchanged in pairs with elements 6b and 7b, with elements 6a and 7a and elements 6b and 7b forming an afocal system, the scale of enlargment of which is preferably reciprocal.

Oscillating mirror 8 and image-forming mirror 10 also form (in conjunction with mirror 9) an afocal system.

The vertical magnification must be varied synchronously to the horizontal magnification, which can be realized by an electronically triggered deflecting device, e.g. a galvanometer scanner.

The invented apparatus, thus, permits varying the size of the examined area (by way of illustration, the size of the examined area of the fundus oculi), i.e. changing the magnification of the whole system.

The combination of two mirrors as image-forming elements and elements determining the magnification yields a number of advantages, such as minimum aberrations, no reflexes, achromatisation including minimum space requirements due to folding of the beam.

It is especially preferred if the image scale between the horizontally deflecting element 5 and the vertically deflecting element 11 assumes the reciprocal value when interchanging mirror 6a and 6b, respectively 7a and 7b, as in that case there is no change in the length of the optical path and mirrors 6a and 6b, respectively 7a and 7b only have to be interchanged, but not shifted, in order to compensate for the length of the optical path.

FIG. 2 shows the section of the invented apparatus, in which sharp focussing and, in particular, refraction compensation occurs. A divider mirror 13 separates the illumination light path 14 and the examination light path 15. In the illustrated preferred embodiment, the separating optical element 13 is a small mirror, which results in a so-called inverted Gullstrand pupil, as was proposed in U.S. Pat. No. 4,213,678.

It is, of course, also possible to employ a normal "Gullstrand pupil" in the manner used in the Japanese patent publication 61-5730, adjacent pupils, in the manner proposed in the Japanese publication 50-138822 or superimposed pupils in the manner described in EP-A-O 145 563.

The device for sharp focussing, respectively for shifting the sharp focus plane as well as for refraction compensation, respectively, for sharp focussing on different planes of the object to be examined set up in accordance with the present invention is provided between divider mirror 13 and the polygonal mirror 5 of the scanning device.

The aforegoing device is provided with interchangeable lenses 1, respectively 1', which by way of illustration are arranged on a revolver 1", a stationary lens 2, two plane mirrors 3a and 3b, which can be shifted jointly in the direction of the arrow including a concave mirror 4. The elements 2 and 4 effect an intermediate image of the pupil plane P", which, in the case of the invented apparatus is placed directly on the reflecting surface of the polygonal mirror 5.

Lens 2 and concave mirror 4 form an afocal system for the correct vision eye. In the event of a vision defect, an appropriate lens 1 of the revolver, respectively lens wheel 1" is arranged in front of lens 2 and the deflecting mirrors 3a and 3b are shifted for fine adjustment in such a manner that the emitted beam runs parallel. In other words the divergence of the beam path is slightly changed by interchanging (respectively omitting) lens 1 so that varying eye refractions can be roughly compensated for. At the same time, by shifting mirrors 3a and 3b, the length of the beam path is altered and fine adjustment is executed.

Furthermore, the invented device for sharp focussing not only permits compensating for varying eye refractions, so that the fundus oculi can always be examined sharply focussed independent of possible vision defects, but also the plane of sharp focus can be shifted.

Such a shifting permits, particularly if a pupil division between illumination and examination light is selected resulting in only shallow focus depth, the examination and reception of various "section planes".

The present invention is described in the preceding section using a preferred embodiment without the intention of limiting the scope of the overall inventive concept, to change the scale of the horizontal image in an image-producing scanning device by interchanging two adjunct image-forming elements and, if required, to adjust the scale of the vertical image by respective triggering of the vertical deflection element. Within this overall inventive concept there are, of course, many different and most varied possible modifications and alterations:

Thus, other optical elements, such as lenses or the like, may be employed. Naturally, the described invented apparatus may be utilized not only for examining the fundus oculi, but also for other purposes for which image-producing scanning devices are otherwise used. However, their use is particularly advantageous for examining the fundus oculi.

Moreover, moveable optical elements can, of course, also be employed instead of interchangeable optical elements 1, so that continuous adjustment becomes possible. Furthermore, just mirrors or just lenses may be utilized as image-forming optical elements instead of mirrors and lenses.

The illustrated arrangement, however, has the advantage that it results in a folding of the light path making a space-saving construction of the invented apparatus possible.

In addition, the invented arrangement may be utilized not only in laser scanning ophthalmoscopes, but also in any equipment for obtaining an image for any desired purpose for sharp focussing and/or for adjusting the sharp-focus plane.

What is claimed is:

1. A scanning ophthalmoscope apparatus for producing an image of an object and, in particular, for examining the eye, having an illumination light source, the light of which can be focussed onto the section of the object to be examined, a scanning device, which generates a scanning movement of the source of the illumination light over the section to be examined and which is provided with beam-deflecting and image-forming optical elements, a detector device, which receives the light reflected from the section to be examined, and an evaluation and synchronization unit, which produces an image of the selected structures of the object from the time-sequential output signal from said detector device, wherein an arrangement of at least two image-forming optical elements is provided in the beam path between said beam-deflecting elements, said arrangement of said at least two imaging-forming optical elements being interchangeable for varying image magnification in a horizontal direction, and said beam deflecting elements include a vertical deflecting device for being triggered for varying vertical image magnification in a vertical direction.

2. A scanning ophtalmoscope apparatus for producing an image of an object and, in particular, for examining the eye, having an illumination light source, the light of which can be focussed onto the section of the object to be examined, a scanning device, which generates a scanning movement of the source of the illumination light over the section to be examined and which is provided with beam-deflecting and image-forming optical elements, a detector device, which receives the light reflected from the section to be examined, and an evaluation and synchronization unit, which produces an image of the selected structures of the object from the time-sequential output signal from said detector device, wherein an arrangement of at least two image-forming optical elements, which are mirrors, is provided in the beam path between said beam-deflecting elements, said arrangement of said at least two mirrors being interchangeable for varying image magnification in a horizontal direction, and said beam deflecting elements include a vertical deflecting device for being triggered for varying vertical image magnification in a vertical direction.

3. A scanning ophthalmoscope apparatus according to claim 1 or 2, wherein said arrangement is provided with two mirrors or lenses, which form an afocal system.

4. A scanning ophthalmoscope apparatus according to claim 3, wherein said image-forming optical elements are Mangin mirrors.

5. An apparatus for producing an image of an object and, in particular, for examining the eye, having an illumination light source, the light of which can be focussed onto the section of the object to be examined, a scanning device, which generates a scanning movement of the source of the illumination light over the section to be examined and which is provided with beam-deflecting and image-forming optical elements, a detector device, which receives the light reflected from the section to be examined, and an evaluation and synchronization unit, which produces an image of the selected structures of the object from the time-sequential output signal from said detector device, wherein an arrangement of at least two image-forming optical elements is provided in the beam path between said beam-deflecting elements, said arrangement of said at least two image-forming optical elements being interchangeable for varying image magnification in a horizontal direction, and said beam deflecting elements include a vertical deflecting device for being triggered for varying vertical image magnification in a vertical direction, wherein two sets of said image-forming optical elements are provided, which are interchangeable by means of a magnifying varier and the scale of enlargement of which is reciprocal.

6. An apparatus for producing an image of an object and, in particular, for examining the eye, having an illumination light source, the light of which can be focussed onto the section of the object to be examined, a scanning device, which generates a scanning movement of the source of the illumination light over the section to be examined and which is provided with beam-deflecting and image-forming optical elements, a detector device, which receives the light reflected from the section to be examined, and an evaluation and synchronization unit, which produces an image of the selected structures of the object from the time-sequential output signal from said detector device, wherein an arrangement of at least two image-forming optical elements is provided in the beam path between said beam-deflecting elements, said arrangement of said at least two image-forming optical elements being interchangeable for varying image magnification in a horizontal direction, and said beam deflecting elements include a vertical deflecting device for being triggered for varying vertical image magnification in a vertical direction, wherein, for sharp focussing, respectively for shifting the site of sharp focus and for compensating refraction, an optical system, which forms an intermediate image of a pupil and which contains at least one interchangeable and/or moveable optical component, is provided between a coupling element separating the illumination light and the reflected light and said scanning device.

7. An apparatus according to claim 6, wherein said optical system is provided with two image-forming optical elements arranged in a stationary manner.

8. An apparatus according to claim 7, wherein said stationary optical elements form an afocal system.

9. An apparatus according to claim 6, wherein a lens is arranged on a lens wheel in an interchangeable manner in the beam path between said scanning device and said coupling element.

10. An apparatus according to one of the claim 9, wherein said lens wheel is provided with a position, in which no additional lens can be inserted in said beam path.

11. An apparatus according to claim 6, wherein said optical system is additionally provided with at least two mirrors, which each deflect the beam path 90° in a plane and which can be jointly shifted in order to alter the length of the optical path.

* * * * *